United States Patent [19]

Danigel et al.

[11] Patent Number: 4,872,753
[45] Date of Patent: Oct. 10, 1989

[54] PROCESS CELL WITH TEMPERATURE COMPENSATION

[75] Inventors: Harald Danigel; Hans-Rudolf Schatzmann, both of Basel, Switzerland

[73] Assignee: Ciba-Geigy Corporation, Ardsley, N.Y.

[21] Appl. No.: 218,193

[22] Filed: Jul. 13, 1988

[30] Foreign Application Priority Data

Jul. 22, 1987 [CH] Switzerland ............ 2774/87

[51] Int. Cl.⁴ ............................. G01N 21/05
[52] U.S. Cl. ................... 356/246; 250/576; 356/410
[58] Field of Search ............ 356/246, 410, 411, 440; 250/343, 576

[56] References Cited

U.S. PATENT DOCUMENTS 3,740,156 6/1973 Heigl et al. ............ 356/246 X
4,786,171 11/1988 Lefebre et al. ............ 356/326

FOREIGN PATENT DOCUMENTS 84070544 6/1984 Fed. Rep. of Germany .
86061720 8/1986 Fed. Rep. of Germany .
722967 2/1955 United Kingdom .

OTHER PUBLICATIONS

Analytical Chemistry, 45 No. 4, (4/73), pp. 802-803.
Applied Spectroscopy 28, No. 3 (1974), pp. 282-283.
Moreau, "Spectrophotometer Cell with Submicron Path Length", p. 1251 (Aug. 1970).
Holden et al, "A Variable Thickness Low Temp. Infra-Red Cell", JOSA 40, 757-760 (11/50).

Primary Examiner—Vincent P. McGraw
Attorney, Agent, or Firm—Harry Falber

[57] ABSTRACT

A process cell (1) for the analysis of liquids, particularly cloudy ones with high light absorption, has a measuring chamber (2) through which flows said liquid, which has two windows (3) lying at a short distance opposite each other for the passage of the measuring light. The latter are held in holding devices (4) which are supported by a common frame (5), which is sufficiently movable relative to the cell housing (6) to be able to perform heat movements. The frame (5) and the holding devices (4) consist of a material with essentially the same coefficient of thermal expansion, so that changes in length of the holding devices (4) occurring upon temperature changes can each time be compensated so that the distance between the two windows (3) practically does not change and thus no changes in the measuring results determined by temperature fluctuations occur.

12 Claims, 1 Drawing Sheet

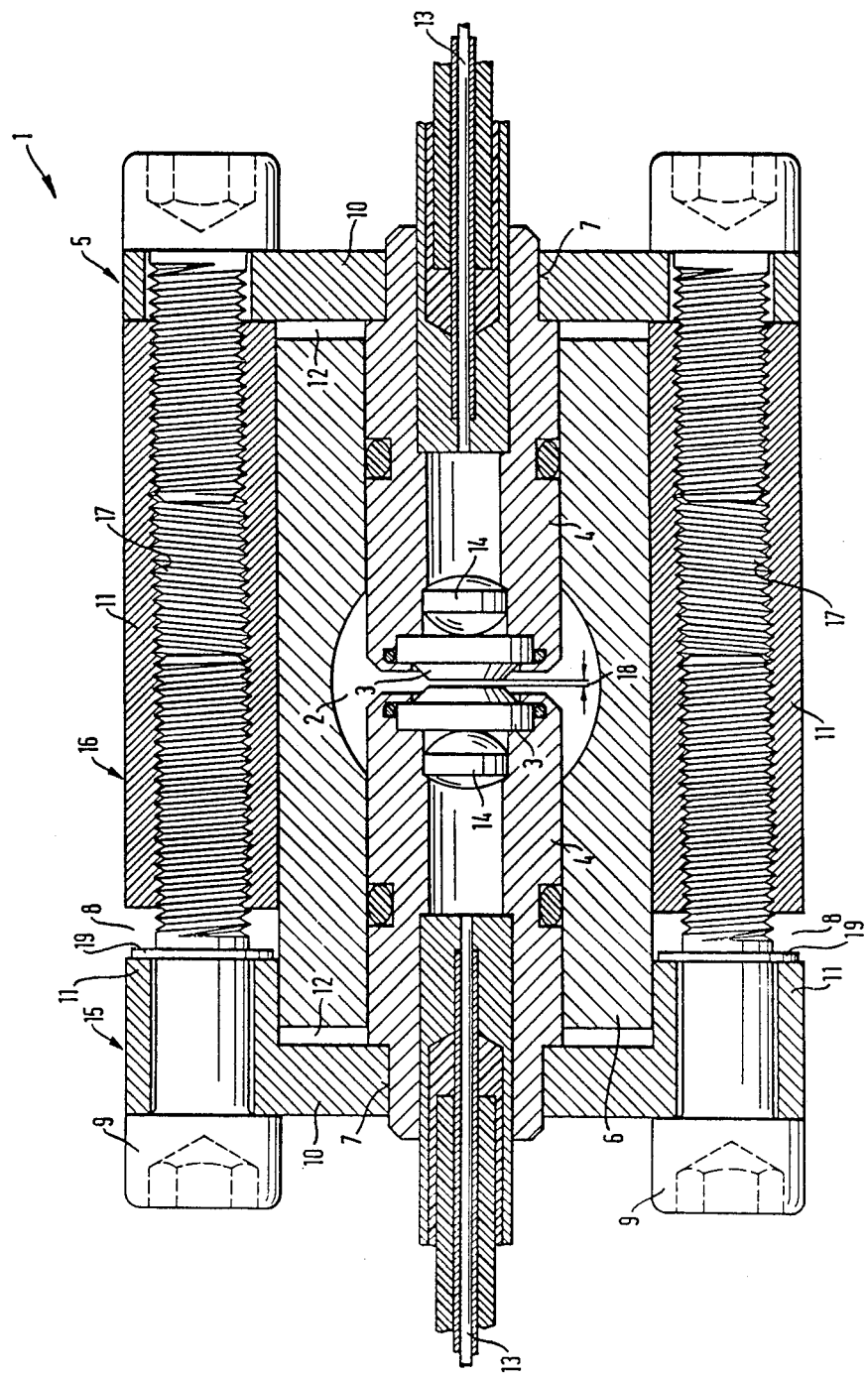

PROCESS CELL WITH TEMPERATURE COMPENSATION

The invention relates to a process cell according to the introductory clause of patent claim 1.

Such process cells are already known in various forms. Some of these measuring devices have adjustability of the distance between the measuring windows, but usually this measuring distance is fixedly pre-set and can only be altered with difficulty or not at all.

Process cells of the latter type are known e.g. from DE-G-84 07 054.4, Analytical Chemistry, Vol. 45, No. 4, April 1973 or DE-G-86 06 172.0. All these devices have two measuring windows adjusted with their plane-parallel light outlet windows at a precisely defined distance from each other, which are held in tubular supports or holding devices. Process cells which have a variable measuring window distance are identical in their principle of construction. The adjustment of the measuring distance takes place e.g. in the devices known from Applied Spectroscopy, Vol. 28, No. 3, 1974 by a piston provided with an internal thread, to which a measuring window is attached, which piston is screwed on to the tube provided with an external thread with the second measuring window. In the device known from GB-A-722,967 the adjustment of the measuring window distance takes place by adjusting screws.

Where possible, such process cells are installed directly in pipes of process plants in order to be able to take on-line measurements of the liquid to be analysed. The distances between the measuring windows are selected to be very small; particularly in the analysis of cloudy, dyed or similar liquids with high light absorption, minimum distances of about $10^{-5}$ m are necessary between the measuring windows emitting measuring light and receiving the measuring light. On the other hand, process cells installed directly in pipes for on-line measurements are subjected to relatively large temperature fluctuations dependent on the temperature of the measuring liquid to be analysed. If the coefficient of thermal expansion of the measuring window supports or holding devices, which is of the magnitude of about $10^{-5} K^{-1}$, is considered, it can be seen very easily that thermal expansions lead to distortions of the measuring results beyond a tolerance limit. All known process cells however have the drawback that they do not comprise any means for compensating for the meauring distance which is altered by the temperature expansion of the measuring window supports or holding devices.

The object of the present invention is therefore to provide a process cell of the above-mentioned type which comprises means to compensate for the change in measuring distance by temperature-related change in length of the measuring window holding devices, in order to guarantee a constant distance between measuring windows under any conceivable process temperatures. In addition, easy adjustability of the distance between measuring windows should be provided.

This problem is solved according to the invention by a process cell according to the characteristics of patent claim 1. Preferred forms are revealed in the dependent claims.

The invention is described in greater detail below with its parts which are essential to it in an embodiment using the drawing. In this case the single FIGURE shows schematically a cross-section through the measuring chamber of the cell with a longitudinal section through the window holders arranged therein and their holder frames.

A process cell which is marked as a whole with 1 serves especially to carry out light measurements on liquids with high light absorption upon their processing or further conveyance. For this purpose the process cell has a measuring chamber 2 through which the liquid flows, which chamber has two windows 3 which upon this measurement lie opposite each other at a short distance approximately in the centre of the measuring chamber 2. Therefore the liquid, on flowing through the measuring chamber 2, arrives beteen said two windows 3, whereupon at one window light is introduced into the measuring chamber 2 and is collected at the opposite window for further conveyance for a spectroscopic examination.

In the example of embodiment shown it is provided for that the two windows 3 are held in holding devices or holders 4 which are supported by a common frame referred to as a whole by 5. The frame 5 is movable relative to the cell housing 6, so that heat movements are possible. It consists of a material with essentially the same coefficients of thermal expansion as the holding devices 4. The two holders 4 with the windows 3 thereby protrude into the flow cross-section of the measuring chamber 2 and leave the latter partly open so that the flow is not too greatly restricted. If a change in length of the holders 4 occurs as the result of temperature changes, there ensues in the same way a similar change in length of the frame 5, so that the distance 18 between the two windows 3 practically does not change and, because of such changes in length of the holding devices 4 determined by temperature fluctuations, no distortions of measuring values exceeding permissible tolerances occur.

It can be clearly seen in the drawing that the window holders 4 penetrate the cell housing 6 approximately radially to the measuring chamber 2 and the frame 5 runs around the outside of the cell housing 6, and that provision is made for the attachment 7 of the holders 4 to the frame 5, which is only indicated schematically, outside the cell housing 6. On this occasion the cell housing 6 is in contact with the frame components 11 arranged parallel to the window holders 4. This ensures that the contrary changes in length of the window holders 4 and said frame components 11 largely keep the distance 18 of each window 3 the same. In this case the cell housing 6 may optionally consist of a material which conducts heat well, in order to produce as identical a temperature as possible both on the holders 4 and on the frame components 11 and thus to result in the desired compensation of changes in distance of the plane-parallel window surfaces facing each other.

In the example of embodiment, the frame 5 consists practically of two parts, which for their part can be subdivided again, a separating point 8 between the two main components 15, 16 of the frame 5 being clearly recognised. This is bridged by means of screws 9 so that said screws 9 belong to the frame components 7 running parallel to the holders 4. The frame components 15,16 connected by said screws 9 are each approximately U-shaped in this case; it does not matter to the effect of the invention that said U-shaped frame components are again each subdivided into a base plate 10 and parts 11 projecting opposite the latter. In this case the screws 9 which are axially immovably fixed to part 15 by a guard ring not only have the advantage that it is very simple to mount the frame 5 around the cell housing 6, but it is clear that, in cooperation with internal threads on the part 16, they also permit a change in the distance of the separation point 8, in so far as the plates 10 for their part leave an intermediate space 12 open with respect to the cell housing 6. Thus the distance 18 between the windows 3 can be adjusted and if necessary changed with the aid of said screws 9, that is to say, set for various liquids. It is helpful for the fastening and adjusting screws 9 for the frame components to be orientated approximately parallel to the window holders 4. Thus changes in the distance 8 have a directly proportional effect on the distance 18 between the windows 3. Thus the window distance can be adjusted in the range of about $10^{-6}$ m to about $10^{-2}$ m.

The fastening and adjusting screws 9 are preferably made of a material which has a coefficient of thermal expansion which is approximately comparable to that of the frame 5.

Other variations of embodiment of the process cell provide for the coefficient of thermal expansion, and thus the materials of the window holding devices 4 and of the multi-part frame 5 along with the fastening and adjusting screws 9 to be variously selected, but the cooperation of the changes in length of the individual components 4, 5, 9 determined by changes in temperature results in compensation of the change in the distance between the measuring windows.

The window members held by the holders 4 may consist for instance of sapphire or quartz. In the example of embodiment light wave guides 13 are connected to said windows 3 by lens systems 14 for supplying light and/or carrying away light, so that both the light source and the measuring apparaus can be housed at a distance from the actual measuring point and thus protected.

We claim:

1. Process cell (1) with a measuring chamber (2) through which flows particularly a cloudy or dyed or similar liquid with high light absorption upon its processing or further conveyance, which chamber has two windows (3) which upon the measurement lie opposite each other at a short distance, light being introduced into the measuring (2) chamber at one window and being received at the opposite window for further conveyance to a preferably spectroscopic investigation in a photometer or the like, characterised in that the two windows (3) are held in holding devices (4), which are supported by a common frame (5) or the like, which frame (5) is movable relative to the cell housing (6), and that the materials of the holding devices (4) and the frame (5) are matched with regard to their coefficients of thermal expansion so that the change in length of the frame (5) which is determined by changes in temperature compensates for the change in length of the holding devices (4) which is determined by changes in temperature.

2. Process cell according to claim 1, characterised in that the two holders (4) with the windows (3) protrude into the flow cross-section of the measuring chamber (2) and leave the latter partly open.

3. Process cell according to claim 1, characterised in that the window holders (4) penetrate the cell housing (6) and the frame (5) runs around the outside of the cell housing (6) and that the attachment (7) of the holders (4) to the frame (5) is provided for outside the cell housing (6).

4. Process cell according to claim 1, characterised in that the cell housing (6) is in contact at leat with the frame components (11) arranged parallel to the window holders (4).

5. Process cell according to claim 1, characterised in that the cell housing (6), at least in the area of the window holders (4) and the frame (5) supporting the latter, consists of a material which conducts heat well.

6. Process cell according to claim 1, characterised in that the frame (5) consists of at least two components which are connected by means of screws (9) or the like, in particular fastening elements with adjustable length.

7. Process cell according to claim 1, characterised in that the fastening and adjusting screws (9) for the frame components are orientated approximately parallel to the window holders (4).

8. Process cell according to claim 1, characterised in that the frame is formed of a material which essentially has the same coefficient of thermal expansion as the holding devices (4) of the windows.

9. Process cell according to claim 7, characterised in that the material of the holding devices (4) of the windows and of the multi-part frame (5) including screws (9) or similar fastening elements are matched with regard to their coefficients of thermal expansion so that the cooperation of the changes in length of the individual components (4, 5, 9) determined by temperature changes compensates for the change in distance between the two windows (3).

10. Process cell according to claim 1, characterised in that the window members held in the holders (4) consist of sapphire or quartz.

11. Process cell according to claim 1, characterised in that light wave guides (13) are connected to the windows (3) optionally by lens systems (14) for supplying light and/or carrying away light.

12. Process cell according to claim 1, characterised in that the frame (5) is interrupted in the region of the screws (9) and with its parts (10) running at right angles to the screws has an intermediate space (12) at the cell housing (6).

* * * * *